United States Patent [19]
Krill et al.

[11] Patent Number: 5,969,176
[45] Date of Patent: Oct. 19, 1999

[54] PROCESS FOR THE PRODUCTION OF TRIMETHYLHYDROQUINONE DIESTERS AND OF TRIMETHYLHYDROQUINONE

[75] Inventors: Steffen Krill, Speyer; Horst Weigel, Rodenbach; Nongyuan Shi, Hainburg; Hans J. Hasselbach; Klaus Huthmacher, both of Gelnhausen; Frank Hübner, Ober-Ramstadt, all of Germany

[73] Assignee: Degussa-Huls AG, Frankfurt, Germany

[21] Appl. No.: 09/249,197

[22] Filed: Feb. 12, 1999

[30] Foreign Application Priority Data

Feb. 12, 1998 [DE] Germany .......................... 198 05 690

[51] Int. Cl.⁶ ............................ C07C 69/76; C07C 69/00
[52] U.S. Cl. ................................. 560/8; 560/129
[58] Field of Search ......................... 560/8, 129

[56] References Cited

FOREIGN PATENT DOCUMENTS

| 0 808 815 | 11/1997 | European Pat. Off. . |
| 0 850 910 | 7/1998 | European Pat. Off. . |
| 0 850 912 | 7/1998 | European Pat. Off. . |

*Primary Examiner*—Raymond Henley, III
*Attorney, Agent, or Firm*—Pillsbury Madison & Sutro LLP

[57] ABSTRACT

An improved process for the production of 2,3,5-trimethylhydroquinone by rearrangement of 4-oxoisophorone (ketoisophorone, 3,5,5-trimethyl-2-cyclohexen-1,4-dione) to yield a trimethylhydroquinone diester and the subsequent saponification thereof. Trimethylhydroquinone is in turn an important starting material for the production of vitamin E.

12 Claims, No Drawings

PROCESS FOR THE PRODUCTION OF TRIMETHYLHYDROQUINONE DIESTERS AND OF TRIMETHYLHYDROQUINONE

FIELD OF INVENTION

This invention relates to an improved process for the production of 2,3,5-trimethylhydroquinone and 2,3,5-trimethylhydroquinone diesters by reaction of 4-oxoisophorone (ketoisophorone, 3,5,5-trimethyl-2-cyclohexen-1,4-dione) with an acylating agent in the presence of catalytic quantities of a superacid to yield a trimethylhydroquinone diester which is optionally subsequently saponified to yield the trimethylhydroquinone.

Trimethylhydroquinone is in turn an important starting material for the production of vitamin E.

BACKGROUND OF THE INVENTION

It is already known (DE 26 46 172 C2) to rearrange ketoisophorone in the gas phase with a zeolite to yield the trimethylhydroquinone. However, the yields of this reaction are only low (50% at 30% conversion) and are thus unsatisfactory for an economic process. In another process (Y. A. Joe, Y. M. Goo, Y. Y. Lee, *Bull. Korean Chem. Soc.* 1991, 12, 253), the rearrangement is performed in a 5% solution in acetic anhydride by the addition of five equivalents of concentrated sulfuric acid. Trimethylhydroquinone esters are obtained in this process at a yield of only 31%, such that this process is also uneconomic. According to a third method (DE-OS 2 149 159), ketoisophorone may be reacted in acetic anhydride in the presence of a protonic acid to yield trimethylhydroquinone diacetate, which is subsequently saponified to yield 2,3,5-trimethylhydroquinone. Disadvantages of this process include the use of

- large quantities of acetic anhydride (5–10 mol./mol. of ketoisophorone),
- large quantities of the catalytic acid (up to 150 mol. %) together with only moderate yields of at most 66%.

SUMMARY OF THE INVENTION

A process has now been found for the production of trimethylhydroquinone (TMHQ) by reaction of ketoisophorone with an acylating agent in the presence of catalytic quantities of a protonic acid and subsequent saponification of the initially formed trimethylhydroquinone ester, which process is characterized in that a protonic acid having a Hammett constant $H_o$ of $<-11.9$ is used. Acids of this type are generally known as "superacidic acids" or "superacids". A description is given in: Olah et al., *Science*, no. 4414, vol. 206, pp. 13 et seq. (1979) and Gillespie et al., *J. Am. Chem. Soc.*, vol. 93, pp. 5083 et seq. (1971). Perchloric acid, fluorosulfonic acid, perfluoroalkane-sulfonic acids of the general formula $$C_nF_{2n+1}SO_3H \qquad (I),$$

in which n is 1–8 may be explicitly mentioned and are suitable for use in the claimed process.

Combinations or mixtures of Brønsted acids with Lewis acids are also suitable. For the purposes of the present invention, these comprise mixtures of various metal halides, such as for example the halides of aluminum, zinc, iron, antimony, arsenic, niobium, tantalum or bismuth with various Brønsted acids.

Also preferred are mixtures of $H_2SO_4/H_3BO_3$ or $HB(HSO_4)_4/H_2SO_4$, mixtures of halosulfonic acid and sulfuric acid. Systems which liberate $H^+AlCl_4^-$ or $H^+BF_4^-$ as the active catalytic species, magic acid ($HSO_3F/SbF_5$) or fluoroantimonic acid ($HF/SbF_5$) have also proved highly suitable.

According to the invention, the acids are in dissolved form. The acids are used in a quantity of 0.1 to 50 wt. %, in particular of 0.5 to 25 wt. %, relative to the final ion. Preferably, >2 to 4 mol., in particular 2.1 to 3 mol. of one of the generally known acylating agents are used per mol. of ketoisophorone.

The acylating agent used according to the invention preferably comprises a carboxylic anhydride, a carboxylic acid chloride or an enol ester, in particular diketene. In particular, a carboxylic anhydride of the general formula

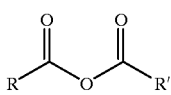

in which R and R' mean an optionally substituted aliphatic, alicyclic or aromatic residue having 1 to 8 carbon atoms, which residue may optionally contain 1 to 3 halogen atoms is used.

Acetic anhydride and acetic acid chloride are particularly preferably used acylating agents. Further suitable acid anhydrides and acid halides are anhydrides and chlorides of propionic acid, butyric acid, isobutyric acid, cyclohexanecarboxylic acid, benzoic acid, chloroacetic acid, trifluoroacetic acid.

In a preferred embodiment, the resultant TMHQ diacetate is saponified without being isolated, optionally after removal of unreacted acetic anhydride by distillation, by the addition of water and/or dilute acid, in particular sulfuric acid, and heating the mixture to boiling. The resultant TMHQ is then filtered out.

It is, however, also possible after the addition of water to separate and isolate the resultant TMHQ diacetate from the reaction mixture, to hydrolyze it in dilute acid, in particular sulfuric acid, in the presence of a phase-transfer agent and to separate the resultant TMHQ, in particular by filtration.

Any organic solvents exhibiting a certain degree of miscibility with water may be used as the phase-transfer agents in the saponification of the isolated trimethylhydroquinone diester too. Acetic acid, n-butanol and n-butyl acetate or mixtures of the stated solvents may particularly advantageously be used.

DETAILED DESCRIPTION OF THE PREFERRED EMBODIMENTS 2,3,5-Trimethylhydroquinone is produced by the process according to the invention in a single-vessel reaction by adding, for example, 0.2 mol. of ketoisophorone dropwise within 1 to 3 hours at 0–60° C. to a mixture of >0.4–0.6 mol. of acetic anhydride and 0.1–50 wt. %, in particular 0.5–25 wt. %, relative to ketoisophorone, of one of the stated very strong acids and subsequently heating the mixture to approx. 25–70° C. for 1 to 7 hours. Residues of the acetic anhydride are then hydrolyzed by adding a sufficient quantity of water. Sulfuric acid, preferably 30%, is optionally added to the resultant suspension and heated to boiling for 1 to 5 hours. A proportion of the solvent is then removed by distillation and replaced by water, the suspension cooled to room temperature and the precipitated trimethylhydroquinone separated.

The precipitated trimethylhydroquinone diester may also be separated after the first addition of water and separately saponified. To this end, the trimethylhydroquinone diester is suspended, for example, in a sufficient quantity of a dilute acid, preferably 30% sulfuric acid, and a phase-transfer agent, such as for example n-butanol, and then heated to boiling for 1 to 7 hours. Distillate is then drawn off and water subsequently added to the bottom product. The trimethylhydroquinone, which has then precipitated, is separated and purified by rewashing.

The following practical Examples illustrate the invention in greater detail.

Considerable advantages over the prior art are achieved by the production according to the invention of 2,3,5-trimethylhydroquinone:

Yields from the process according to the invention are up to approx. 25% higher than in the cited literature and are between 85 and 95%.

The required quantities of catalyst are 0.1 to 50%, in comparison with up to 150% in the literature.

Only >2 to 4 mol. of a carboxylic anhydride are required per mol. of ketoisophorone, in comparison with 5 to 10 mol. in the literature.

Saponification of the isolated trimethylhydroquinone diester with aqueous acid preferably proceeds simply in the presence of a phase-transfer agent.

EXAMPLE 1

0.34 g (2.3 mmol.) of trifluoromethanesulfonic acid are added to 61 g (0.6 mol.) of acetic anhydride, and 30.5 g (0.2 mol.) of ketoisophorone (98%) are then added dropwise within 30 minutes with exclusion of moisture. The temperature is maintained below 50° C. by cooling. Conversion is taken to completion by maintaining the temperature at 45 to 50° C. for a further 2 hours. The temperature is then reduced to 20° C., wherein crystals form. 125 ml of water are added to complete the crystallization of the trimethylhydroquinone diacetate. The solid is separated by suction filtration and heated to boiling for 4 hours in a mixture of 100 ml of 30% sulfuric acid and 15 ml of n-butanol. 80 ml of a mixture of acetic acid, n-butanol and water are then removed by distillation, 100 ml of water are added and the suspension cooled to 20° C. The precipitated trimethylhydroquinone is separated by suction filtration, washed with water and dried under a vacuum at 55° C.

Yield: 27.3 g (89.7% of theoretical)

Purity: 98.5% (HPLC)

EXAMPLE 2

133 mg (2.15 mmol.) of boric acid and 860 mg (8.6 mmol.) of 98% sulfuric acid are stirred for 30 minutes in 30.6 g (0.3 mol.) of acetic anhydride, and 15.5 g (0.1 mol.) of ketoisophorone (98%) are then added dropwise. The temperature is maintained below 35° C. by cooling. The temperature is then maintained at 30° C. for 5 hours, wherein 98.6% of the keto compound react. Analysis (HPLC) reveals a content of 45.2% trimethylhydroquinone, corresponding to a selectivity of 91.5%.

EXAMPLE 3

121 mg (1.95 mmol.) of boric acid and 1.0 g (10 mmol.) of sulfuric acid (98%) are initially introduced into 35.7 g (0.35 mol.) of acetic anhydride with exclusion of moisture and 15.5 g (0.1 mol.) of ketoisophorone (98%) are added dropwise with stirring at 30° C. Stirring is continued for a further 4.5 hours at 30° C. 70 g of 30% aqueous sulfuric acid are then added and hydrolysis performed by refluxing. Once 40 ml (of acetic acid, water) have been removed by distillation, the mixture is diluted with 50 ml of water and cooled to 20° C. The crystallized trimethylhydroquinone is separated by suction filtration, washed with water and dried under a vacuum.

Yield: 13.9 g (91.4% of theoretical) of trimethylhydroquinone

Purity: 95.8% (HPLC)

EXAMPLE 4

31.4 g (0.4 mol.) of acetyl chloride and 0.3 g of trifluoromethanesulfonic acid are initially introduced and 12.4 g (0.08 mol.) of ketoisophorone (98%) are added dropwise, wherein HCl escapes and the temperature rises from 25 to 32° C. After one hour at 50° C., conversion of the ketoisophorone is complete. The excess acetyl chloride is removed by distillation under reduced pressure and the remaining residue is stirred together with 50 ml of iced water. After suction filtration, washing with water and drying at 45° C. under a vacuum, 17.6 g of trimethylhydroquinone diacetate (93.1% of theoretical) are obtained at a purity of 93.9% (HPLC).

EXAMPLE 5

0.26 ml (4.6 mmol.) of fluorosulfonic acid are added to 38.8 g (0.38 mol.) of acetic anhydride with exclusion of moisture and 23.3 g (0.15 mol.) of ketoisophorone (98%) are added dropwise. The mixture is heated to 50–60° C. until in excess of 99% of the ketoisophorone has reacted. The clear solution is then combined with 130 g of iced water and adjusted to pH 6 with 40% aqueous sodium hydroxide solution. The crystallized trimethylhydroquinone diacetate is separated by suction filtration at 5° C. and washed with water. After drying under a vacuum at 50° C., 34.7 g are obtained, corresponding to a yield of 98.0% of theoretical. Purity is 94.7% (HPLC).

EXAMPLE 6

20 ml of concentrated sulfuric acid are stirred for 20 minutes with 4.8 g of boric acid, then 20 ml of oleum (65% $SO_3$) are added dropwise with cooling.

7.6 g of this borosulfuric acid are added to 25.5 g (0.25 mol.) of acetic anhydride, and 15.5 g (0.1 mol.) of ketoisophorone (98%) are added dropwise at 40° C. After 2.5 hours at this temperature, conversion is complete. Selectivity for the formation of trimethylhydroquinone diacetate is 93.1% (GC). After hydrolysis, as described in Example 3, 14.1 g of trimethylhydroquinone (92.8% of theoretical) are obtained at a purity of 96.0% (HPLC).

What is claimed is:

1. A process for the production of trimethylhydroquinone diesters (2)

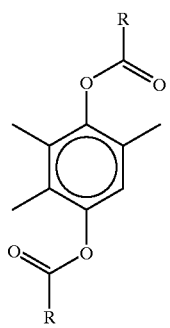

(2)

in which R represents an optionally substituted aliphatic, alicyclic or aromatic hydrocarbon residue and 2,3,5-trimethylhydroquinone (3)

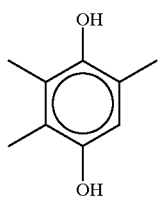

(3)

by reaction of 4-oxoisophorone (1)

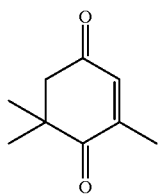

(1)

with an acylating agent in the presence of catalytic quantities of a protonic acid and optionally subsequent saponification of the initially formed trimethylhydroquinone ester, comprising:

using as the protonic acid an acid having a Hammett constant $H_o$ of $\leq -11.9$ (superacidic acids).

2. A process according to claim 1, comprising:

using perchloric acid, fluorosulfonic acid or perfluoroalkane-sulfonic acids of the general formula

in which n is 1–8 as the protonic acid.

3. A process according to claim 1, comprising:

using mixtures of Lewis acids and Brønsted acids as the protonic acid.

4. A process according to claim 1, comprising:

using mixtures of $H_2SO_4/H_3BO_3$ or $HB(HSO_4)_4/H_2SO_4$ as the protonic acid.

5. A process according to claim 1, comprising:

using systems which liberate $H^+AlCl_4$ or $H^+BF^4$ as the protonic acid.

6. A process according to claim 1, comprising:

using magic acid ($HSO_3F/SbF_5$) or fluoroantimonic acid ($HF/SbF_5$) as the protonic acid.

7. A process according to claim 1, comprising:

using the acid in a quantity of 0.1 to 50 wt. %, relative to the final ion.

8. A process according to claim 1, comprising:

using >2 to 4 mol. of the acylating agent per mol. of ketoisophorone.

9. A process according to claim 1, comprising:

using acetic anhydride, diketene or acetyl chloride as the acylating agent.

10. A process according to claim 1, comprising:

saponifying the resultant TMHQ diacetate without being isolated, optionally after removal of unreacted acetic anhydride by distillation, by the addition of water and/or dilute acid, and separating the resultant TMHQ.

11. A process according to claim 1, comprising:

isolating the resultant TMHQ diacetate from the reaction mixture, optionally subsequently saponifying using dilute acid in the presence of a phase-transfer agent, and separating the resultant TMHQ.

12. A process according to claim 1, comprising:

using acetic acid, n-butanol, n-butyl acetate or mixtures thereof as the phase-transfer agent.

* * * * *